(12) United States Patent
Zuber et al.

(10) Patent No.: US 12,263,242 B2
(45) Date of Patent: *Apr. 1, 2025

(54) CONTAINER WITH PARTICLES FOR USE WITH INHALER

(71) Applicant: PHILIP MORRIS PRODUCTS S.A., Neuchâtel (CH)

(72) Inventors: Gerard Zuber, Boulens (CH); Judith Waller, Ostersund (SE)

(73) Assignee: Philip Morris Products S.A., Neuchâtel (CH)

( * ) Notice: Subject to any disclaimer, the term of this patent is extended or adjusted under 35 U.S.C. 154(b) by 386 days.

This patent is subject to a terminal disclaimer.

(21) Appl. No.: 16/623,923

(22) PCT Filed: Jun. 26, 2018

(86) PCT No.: PCT/IB2018/054720
§ 371 (c)(1),
(2) Date: Dec. 18, 2019

(87) PCT Pub. No.: WO2019/003118
PCT Pub. Date: Jan. 3, 2019

(65) Prior Publication Data
US 2020/0196674 A1 Jun. 25, 2020

(30) Foreign Application Priority Data
Jun. 28, 2017 (EP) ..................................... 17178416

(51) Int. Cl.
*A24F 40/42* (2020.01)
*A24B 15/16* (2020.01)
(Continued)

(52) U.S. Cl.
CPC ............ *A61K 9/0075* (2013.01); *A24B 15/16* (2013.01); *A24B 15/403* (2013.01); *A24F 40/20* (2020.01);
(Continued)

(58) Field of Classification Search
None
See application file for complete search history.

(56) References Cited

U.S. PATENT DOCUMENTS

| 3,634,582 A | 1/1972 | Hartley et al. |
| 6,234,169 B1 | 5/2001 | Bulbrook et al. |

(Continued)

FOREIGN PATENT DOCUMENTS

| EP | 2614848 A1 | 7/2013 |
| RU | 2463085 | 10/2012 |

(Continued)

OTHER PUBLICATIONS

Capsuline, "Which Capsule is Right For You: A Guide to Choosing the Right Capsule Size for Your Needs," Published Dec. 6, 2016, https://capsuline.com/blogs/capsuline-blog/which-capsule-is-right-for-you-a-guide-to-choosing-the-right-capsule-size-for-your-needs (Year: 2016).*

(Continued)

*Primary Examiner* — Philip Y Louie
*Assistant Examiner* — Sonny V Nguyen
(74) *Attorney, Agent, or Firm* — Mueting Raasch Group (57) ABSTRACT

A container containing a powder system including a first plurality of particles having a particle size of about 10 micrometers or less, and a second plurality of particles having a particle size of about 20 micrometers or greater, and a single aperture extending through the container. A system including an inhaler article and the container is disclosed also.

20 Claims, 3 Drawing Sheets (51) Int. Cl.

| | |
|---|---|
| *A24B 15/40* | (2006.01) |
| *A24F 40/20* | (2020.01) |
| *A24F 42/20* | (2020.01) |
| *A24F 42/60* | (2020.01) |
| *A61K 9/00* | (2006.01) |
| *A61M 15/00* | (2006.01) |

(52) U.S. Cl.
CPC ............. *A24F 40/42* (2020.01); *A24F 42/20* (2020.01); *A24F 42/60* (2020.01); *A61M 15/003* (2014.02); *A61M 15/0035* (2014.02); *A61M 2202/064* (2013.01); *A61M 2206/16* (2013.01)

(56) References Cited

U.S. PATENT DOCUMENTS

| | | | |
|---|---|---|---|
| 6,732,732 B2 | 5/2004 | Edwards et al. | |
| 8,037,880 B2 | 10/2011 | Zhu et al. | |
| 8,573,197 B2 | 11/2013 | Axford et al. | |
| 10,070,666 B2 | 9/2018 | Buehler et al. | |
| 10,149,844 B2 | 12/2018 | Stenzler et al. | |
| 10,912,334 B2 | 2/2021 | Zinovik et al. | |
| 11,224,594 B2 | 1/2022 | Stenzler et al. | |
| 2003/0150453 A1 | 8/2003 | Edwards et al. | |
| 2004/0156792 A1 | 8/2004 | Tarara et al. | |
| 2006/0254583 A1 | 11/2006 | Deboeck et al. | |
| 2007/0235029 A1 | 10/2007 | Zhu et al. | |
| 2011/0277752 A1 | 11/2011 | Cheu et al. | |
| 2014/0130800 A1* | 5/2014 | Seeney ............. | A61M 15/0065 128/203.15 |
| 2014/0015078 A1 | 6/2014 | Ellwanger et al. | |
| 2014/0150787 A1* | 6/2014 | Ellwanger ......... | A61M 15/0041 30/366 |
| 2014/0182587 A1* | 7/2014 | Dunne ............. | A61M 15/0025 128/203.15 |
| 2017/0035108 A1 | 2/2017 | Zinovik et al. | |
| 2017/0071856 A1 | 3/2017 | Stenzler et al. | |
| 2017/0071929 A1 | 3/2017 | Stenzler et al. | |
| 2017/0135397 A1 | 5/2017 | Buehler et al. | |
| 2017/0172996 A1* | 6/2017 | Stenzler ............... | A61K 9/0075 |

FOREIGN PATENT DOCUMENTS

| | | |
|---|---|---|
| WO | WO 2015/166350 A2 | 11/2015 |
| WO | WO 2015/173648 A2 | 11/2015 |
| WO | WO 2015/198067 A1 | 12/2015 |
| WO | 20170048974 | 3/2017 |
| WO | WO 2017/048972 A1 | 3/2017 |
| WO | WO 2017/109625 A1 | 6/2017 |
| WO | WO 2017/109626 A1 | 6/2017 |
| WO | WO 2017/109678 A1 | 6/2017 |
| WO | WO 2018/100461 A1 | 6/2018 |

OTHER PUBLICATIONS

Extended European Search Report for EP 17178416.8, issued by the European Patent Office on Dec. 22, 2017; 7 pgs.

International Search Report and Written Opinion for PCT/IB2018/054720, issued by the European Patent Office on Sep. 19, 2018; 16 pgs.

International Preliminary Report on Patentability for PCT/IB2018/054720, issued by the European Patent Office on Aug. 6, 2019; 17 pgs.

Cohen et al., "GRAS Flavoring Substances," 27. *GRAS Flavoring Substances. Food Technology for Flavoring Extract Manufacturers Association*, Aug. 2015:69(8):40-59.

Hall, R.L. & Oser, B.L., "Recent Progress in the Consideration of Flavoring Ingredients under the Food Additive Amendments 3. GRAS substances," *Food Technology*, Feb. 1965: p. 151-197.

Japanese Office Action for JP 2019-569310 issued by the Japanese Patent Office on Mar. 2, 2022; 8 pgs. including English translation.

Behara et al., "Development of High Efficiency Dry Powder Inhaler: Effects of Capsule Chamber Design and Inhaler Surface Modifications," Feb. 2014;31(2):360-372.

Russian Office Action for RU 2019141658 issued by the Patent office of the Russian Federation on Feb. 8, 2022; 29 pgs. including English translation.

Brazilian Office Action for BR112019025635-0 issued by the Brazilian Patent Office on Jun. 14, 2022, 7 pgs.

Rissler et al., "Deposition efficiency of inhaled particles (15-5000 nm) related to breathing pattern and lung function: an experimental study in healthy children and adults," Particle and Fibre Toxicology, 2017;14:10: 12 pgs.

Russian Office Action for RU 2019141658 issued by the Patent office of the Russian Federation on Jul. 12, 2022; 24 pgs. including English translation.

Chinese Office Action for CN Application No. 201880037255.1 issued by the Chinese patent Office on Feb. 13, 2023; 27 pgs. Including English translation.

Second Office Action for Chinese Application No. 201880037255.1 issued by the Chinese Patent Office, Sep. 4, 2023; 21 pgs. Including English translation.

* cited by examiner

CONTAINER WITH PARTICLES FOR USE WITH INHALER

This application is the § 371 U.S. National Stage of International Application No. PCT/IB2018/054720, filed 26 Jun. 2018, which claims the benefit of European Application No. 17178416.8, filed 28 Jun. 2017, the disclosures of which are incorporated by reference herein in their entireties.

This disclosure relates to a container with particles for use with an inhaler. The container may hold nicotine particles. The nicotine particles are advantageously suitable for inhalation that may mimic a conventional smoking regime when utilized with the inhaler.

Dry powder inhalers (DPI) are known and are used to treat respiratory diseases by delivering a dry powder comprising a pharmaceutically active compound, in aerosol form through inhalation to airways of patients. In pharmaceutical dry powders, the active pharmaceutical ingredient (API) is usually agglomerated on the surface of larger carrier particles, such as lactose for example. DPI's operate through complex mechanisms to ensure such agglomerates disperse, break up or disaggregate before the API is inhaled into the lungs.

However, dry powder inhalers may not be suitable to provide dry powder particles to the lungs in a manner consistent with conventional smoking regimes. For example, dry powder inhalers often strive to provide an entire dry powder dose or the entire contents of the container in a single breath. In contrast, conventional smoking regimes involve a number of comfortable puffs. Nicotine particles tend to suffer from drawbacks that may present challenges for delivery to the lungs at inhalation at air flow rates associated with conventional smoking regimes. Nicotine particles with a mass median aerodynamic diameter (MMAD) of less than about 10 micrometres tend to be increasingly thermodynamically unstable due to a high surface area to volume ratio, which provides an increasing surface free energy with the decreasing particle size, and consequently increases the tendency of particles to agglomerate and increases the strength of the agglomerate. This may lead to handling and storage concerns of the nicotine particle compositions. In addition, it may be difficult to deliver a uniform series of doses of particles from a single container utilizing only inhalation airflow. It may also difficult to fully empty particles from the single container in this manner.

It would be desirable to provide a container or capsule with a powder system that delivers a series of particle doses at inhalation or air flow rates that are associated with conventional smoking regimes. It would be desirable to provide a container or capsule with a powder system that delivers a series of particle doses with limited variation of nicotine delivery at inhalation or air flow rates that are associated with conventional smoking regimes. It would be desirable to remove all, or substantially all, of the powder system from the container or capsule at inhalation or air flow rates that are associated with conventional smoking regimes. It would be desirable to provide system that includes the container or capsule with a powder system and an inhaler article that has a form similar to a conventional cigarette. It would also be desirable that this system be simple to manufacture and convenient to use by a consumer.

This disclosure relates to a container containing a powder system. The powder system includes a first plurality of particles having a particle size of about 10 micrometers or less, and a second plurality of particles having a particle size of about 20 micrometers or greater. A single aperture extends through the container. The powder system may include a weight ratio of the first plurality of particles to second plurality of particles of about 2:1 to about 6:1, or about 3:1 to about 5:1, preferably about 4:1.

This disclosure relates to a system including an inhaler article having a cavity for receiving a container described herein, and a piercing element for forming a single aperture in the container.

The container may be a conventional capsule enclosing the powder system. The capsule may be a conventional capsule having an obround shape. The powder system may suitable for inhalation that may mimic a conventional smoking regime when utilized with an inhaler.

The container or capsule includes only a single hole or aperture extending through the container or capsule where inhalation air enters the cavity of the container or capsule and particle entrained inhalation air also exits the container or capsule through the same single hole or aperture. The first plurality of particles may comprise nicotine. The single aperture may be sized to provide a fractional and substantially uniform amount of particles comprising nicotine with each puff or inhalation when the capsule is utilized with an inhaler article.

The container or capsule may include one or more apertures. However, the one or more apertures may only be present one end or side (the same end or side) of the container or capsule. For example, a capsule may have only one aperture extending through one end cap of the capsule, preferably the upstream endcap of the capsule. The capsule may have two or more apertures extending through one end cap of the capsule, preferably the upstream endcap of the capsule. The capsule may have one or more apertures extending through a longitudinal wall of the capsule. The open surface area of the one or more apertures may be in a range from about 0.1% to about 0.5% of the total surface area of the container or capsule.

The second plurality of particles may contain a flavor component, such as menthol. The powder system may include the first plurality of particles and the second plurality of particles at a certain weight ratio, such as from about two to about six parts by weight of the first plurality of particles for every one part of the second plurality of particles, or from about three to about five parts by weight of the first plurality of particles for every one part of the second plurality of particles, or preferably about four parts by weight of the first plurality of particles for every one part of the second plurality of particles.

Advantageously, the powder system in combination with the single aperture provides a series of uniform particle doses at inhalation or air flow rates that are associated with conventional smoking regimes. In addition, all, or substantially all, of the powder system may be dispensed from the container or capsule at inhalation or air flow rates that are associated with conventional smoking regimes. The relative sizes of the single aperture and powder system and stable rotation of the container or capsule may provide uniform entrainment of a portion or a fraction of powder system from the container or capsule over five or more, or ten or more, or 25 or more, or 40 or more comfortable inhalations or "puffs" by a consumer.

Advantageously, the powder system described herein may provide improved nicotine delivery from the container or capsule when used in an inhaler article. The powder system may provide a consistent and reliable nicotine delivery throughout the use of the device, for example for up to 10 puffs, up to 20 puffs, up to 40 puffs, or up to 50 puffs utilizing the same container or capsule.

Advantageously, the powder system described herein may be stable over time and forms a flowable composition. The powder system can deliver an improved delivery of nicotine into the lungs of the user at inhalation or air flow rates that are within conventional smoking regime inhalation or air flow rates.

Advantageously, the inhaler article and container system has a similar form to a conventional cigarette. In addition, this system may be simple to manufacture and convenient to use by a consumer.

The container or capsule, powder system and inhaler article described herein may provide particles to the lungs at inhalation or air flow rates that are within conventional smoking regime inhalation or air flow rates. A consumer may take a plurality of inhalations or "puffs" where each "puff" delivers a uniform fractional amount of dry powder contained within a container or capsule contained within the capsule cavity of the inhaler article. This inhaler may have a form similar to a conventional cigarette and may mimic the ritual of conventional smoking and may provide a pleasure or entertainment form of nicotine delivery. This inhaler may be simple to manufacture and convenient to use by a consumer.

Air flow management through the capsule cavity may cause the capsule or container to rotate during inhalation and consumption. The container or capsule contains a powder system comprising a first plurality of small particles and a second plurality of large particles. Rotation of the pierced container or capsule may suspend and aerosolize the powder system released from the pierced capsule into the inhalation air moving through the inhaler article. The second plurality of particles may assist in transporting the first plurality of particles into the lungs of the user while the second plurality of particles preferentially remain in the mouth or buccal cavity of the user.

Described herein, among other things, are nicotine powder formulations, containers for nicotine powder formulations, and inhaler articles. The nicotine powder formulations described herein may be used with any suitable container, such as the containers described herein. The containers described herein, such as the capsules described herein, may be used with any suitable inhaler article, such as the inhaler articles described herein.

The term "nicotine" refers to nicotine and nicotine derivatives in any form, including but not limited to, a free-base nicotine, nicotine salt, or in a matrix such as a sugar matrix or organometallic complex.

The term "amino acid" refers to a single unmodified or modified amino acid moiety, preferably unmodified.

The phrase "fluid energy milling" refers to particle size reduction by colliding particle streams. Fluid energy milling includes air jet milling or jet milling.

The size of a particle, stated herein, preferably refers to the aerodynamic diameter of the particle. The aerodynamic diameter of a powder system is preferably measured with a cascade impactor. The term "MMAD" refers to the mass median aerodynamic diameter. Particle size may also be given as "VMD" which refers to volume mean diameter. Particle size distribution may be given as a size under which a certain percentage (e.g., 10%, 50%, or 90%, by volume) of particles falls.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg. 151-197, and in the GRAS flavoring substances 27 S. M. Cohen et al., Food Technology August 2015 pg. 40-59, and intervening GRAS Flavoring Substances publications 4 to 26. For this disclosure, nicotine is not considered as a flavourant or flavour.

The container or capsule contains a powder system of a first plurality of particles having a particle size of about 10 micrometers or less, and a second plurality of particles having a particle size of about 20 micrometers or greater. The container or capsule contains a powder system a first plurality of particles having a particle size of about 5 micrometers or less, and a second plurality of particles having a particle size of about 50 micrometers or greater. At least 50%, or at least 75%, or at least 90% of the first plurality of particles may have a particle size of about 5 micrometers or less, or about 3 micrometers or less. At least 50%, or at least 75%, or at least 90% of the second plurality of particles may have a particle size of about 50 micrometers or greater, or about 75 to about 200 micrometers.

The powder system may comprise a weight ratio of the first plurality of particles to second plurality of particles of about 1:1 to about 10:1, or about 2:1 to about 8:1, or about 2:1 to about 6:1, or about 3:1 to about 5:1, preferably about 4:1. By carefully selecting the weight ratio of the first plurality of particles to second plurality of particles, it is possible to further improve the full delivery of the content of the container over a series of inhalation containing a similar amount of powder.

The container or capsule may include one and only one aperture extending through the container or capsule. The container or capsule may include less than two apertures extending through the container or capsule. The container or capsule does not comprise more than one aperture extending through the container or capsule. Air may flow into and out of the same single aperture.

The container or capsule may include one or more apertures. However, the one or more apertures may only be present one end or side (the same end or side) of the container or capsule. For example, a capsule may have only one aperture extending through one end cap of the capsule, preferably the upstream endcap of the capsule. The capsule may have two or more apertures extending through one end cap of the capsule, preferably the upstream endcap of the capsule. The capsule may have one or more apertures extending through a longitudinal wall of the capsule.

The single aperture or the one or more apertures may have a diameter from about 0.1 mm to about 4 mm or from about 0.2 mm to about 2 mm, or from about 0.5 mm to about 1.5 mm, or from about 0.8 mm to about 1.2 mm, or from about 0.9 mm to about 1.1 mm, or about 1 mm. The single aperture or the one or more apertures may have an open surface area from about 0.1 mm$^2$ to about 2 mm$^2$, or from about 0.5 mm$^2$ to about 1 mm$^2$, or from about 0.7 mm$^2$ to about 0.9 mm$^2$. The open surface area of the single aperture or the one or more apertures may be in a range from about 0.1% to about 0.5%, or from about 0.2% to about 0.5%, or from about 0.3% to about 0.4% of the total surface area of the container or capsule.

The single aperture may be incident with a longitudinal axis of the capsule. When the capsule is placed in the inhaler article and pierced, airflow through the dry powder inhaler may cause the capsule to rotate about the longitudinal axis of the capsule.

The container or capsule may define an internal volume referred as the internal volume of the capsule. The internal volume of the capsule may be from 0.02 mL to about 3 mL or from about 0.1 mL to about 0.9 mL or from about 0.2 mL to about 0.5 mL, or from about 0.25 mL to about 0.3 mL. The single aperture or the one or more apertures may have an open surface area of from about 0.7 $mm^2$ to about 7 $mm^2$ per mL of internal volume of the capsule or from about 1 $mm^2$ to about 3 $mm^2$ per mL of internal volume of the capsule.

The container or capsule may hold or contain at least about 5 mg of a powder system, or from about 10 mg to about 200 mg, or from about 20 mg to about 100 mg, or from about 20 mg to about 80 mg, or from 40 mg to 70 mg, or from 40 mg to 60 mg, or about 50 mg of the powder system. The container or capsule may contain enough powder system to provide at least 2 inhalations or "puffs", or at least about 10 inhalations or "puffs", or at least about 20 inhalations or "puffs". The container or capsule may contain enough powder system to provide from about 5 to about 50 inhalations or "puffs", or from about 20 to about 50 inhalations or "puffs".

The powder system may comprise from about 50 wt % to about 95 wt %, or from about 65 wt % to about 90 wt %, or from about 75 wt % to about 85 wt %, or preferably about 80 wt % of a first plurality of particles.

The powder system may comprise from about 50 wt % to about 5 wt %, or from about 45 wt % to about 10 wt %, or from about 25 wt % to about 15 wt %, or preferably about 20 wt % of a second plurality of particles.

The powder system may comprise from about 50 wt % to about 95 wt %, or from about 65 wt % to about 90 wt %, or from about 75 wt % to about 85 wt %, or preferably about 80 wt % of a first plurality of particles having a particle size of about 10 micrometers or less, and a nicotine content of 1 wt % or more.

The powder system may comprise from about 50 wt % to about 5 wt %, or from about 45 wt % to about 10 wt %, or from about 25 wt % to about 15 wt %, or preferably about 20 wt % of a second plurality of particles having a particle size of about 20 micrometers or more, and a nicotine content of 0.1 wt % or less.

The powder system may comprise from about 5 mg to about 100 mg, or from about 20 mg to about 80 mg, or from about 30 mg to about 50 mg, or preferably about 40 mg of a first plurality of particles.

The powder system may comprise from 1 mg to about 100 mg, or from about 5 mg to about 50 mg, or from about 5 mg to about 20 mg, or preferably about 10 mg of a second plurality of particles.

The powder system may comprise from about 5 mg to about 100 mg, or from about 20 mg to about 80 mg, or from about 30 mg to about 50 mg, or preferably about 40 mg of a first plurality of particles having a particle size of about 10 micrometers or less, and a nicotine content of 1 wt % or more.

The powder system may comprise from about 1 mg to about 100 mg, or from about 5 mg to about 50 mg, or from about 5 mg to about 20 mg, or preferably about 10 mg of a second plurality of particles having a particle size of about 20 micrometers or more, and a nicotine content of 0.1 wt % or less.

The powder system may comprise a weight ratio of the first plurality of particles having a particle size of about 10 micrometers or less and a nicotine content of 1 wt % or more to second plurality of particles having a particle size of about 20 micrometers or more and a nicotine content of 0.1 wt % or less, of about 2:1 to about 6:1 or about 3:1 to about 5:1, preferably about 4:1.

The container or capsule may rotate about its longitudinal or central axis when air flows through the inhaler article. The capsule may be formed of an airtight material that may be pierced or punctured by a piercing element that may be separate or combined with the inhaler. The capsule may be formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxypropylmethylcellulose (HPMC). The capsule may be a size 0 to size 5 capsule, or a size 2 capsule, or a size 3 capsule, or a size 4 capsule.

A separate piercing element, such as a metal or rigid needle, may form a single aperture (only a single aperture) through the capsule received in the capsule cavity. The piercing element may pass through the resealable element sealing the piercing channel on the end cap.

The powder system of the present disclosure may be formed by spray drying a liquid mixture to form a first plurality of particles. The liquid mixture comprises nicotine. The liquid mixture may also comprise a sugar, or an amino acid, or both a sugar and amino acid. Spray drying the liquid mixture may form a homogenous first plurality of particles. The powder system also includes a second plurality of particles that have a particle size that is larger than the first plurality of particles. For example, the particle size of the second plurality of particles may be greater than that of the first plurality of particles. The second plurality of particles may include nicotine or may be free of nicotine. The powder system may be formed by combining the first plurality of particles with the second plurality of particles at the desired weight ratio. An inhalation delivery consumable element may contain the powder system described herein.

The first plurality of particles may be milled (such as with a fluid energy mill) to reduce the size distribution of the first plurality of particles. The first plurality of particles may have a particle size distribution where about 90% (by volume) of the plurality of particles have a particle size of less than about 3 micrometres, and about 50% of the plurality of particles have a particle size of less than about 1.5 micrometres, and about 10% of the third plurality of particles having a particle size of less than about 0.65 micrometres. The percentages relating to particle size distribution described herein are based on particle volume (% by volume) unless mass or weight basis is specifically stated.

The first plurality of particles may have a mass median aerodynamic diameter of about 10 micrometres or less, or in a range from about 0.5 micrometres to about 6 micrometres, or in a range from about 1 micrometres to about 5 micrometres or in a range from about 1 micrometres to about 4 micrometres. The mass median aerodynamic diameter is preferably measured with a cascade impactor.

The first plurality of particles may comprise about 50%, or about 75%, or about 80%, or about 90%, or about 95%, or about 98% of particles having an aerodynamic diameter of about 5 micrometres or less. The first plurality of particles may comprise at least about 50% of particles having an aerodynamic diameter of about 3 micrometres or less. The first plurality of particles may comprise at least about 10% of particles having an aerodynamic diameter of about 0.85 micrometres or less. Substantially all particles of the first plurality of particles may have an aerodynamic diameter in a range from about 500 nanometers to about 5 micrometres.

The nicotine component of the particles forming the first plurality of particles may be a free base nicotine, a nicotine salt, or a combination thereof. The nicotine component may be a nicotine salt formed by combining nicotine or nicotine free base with an acid. The acid may be a stoichiometric amount of acid to the nicotine free base, or a stoichiometric excess of acid may be combined with the nicotine free base, or a stoichiometric excess of nicotine free base may be combined with the acid. A free base nicotine may be utilized without the addition of an acid.

The acid may be an organic acid, an inorganic acid, or a Lewis acid. Non-limiting examples of inorganic acids are hydrochloric, hydrobromic, hydroiodic, nitric, sulfuric, phosphoric, acetic, hexafluorophosphoric, and the like. Non-limiting examples of organic acids are levulinic, citric, gluconic, benzoic, propionic, butyric, sulfosalicylic, maleic, lauric, malic, fumaric, succinic, tartaric, amsonic, pamoic, mesylic, aspartic, formic, acetic, propionic, succinic, camphorsulfonic, fumaric, isethionic, lactic, mucic, para-toluenesulfonic, glycolic, glucuronic, maleic, furoic, glutamic, benzoic, anthranilic, salicylic, phenylacetic, pyruvic, mandelic, embonic (pamoic), methanesulfonic, ethanesulfonic, pantothenic, benzenesulfonic (besylate), stearic, sulfanilic, alginic, galacturonic, and the like. Non-limiting examples of Lewis acids are zinc chloride or zinc bromide ($ZnCl_2$/$ZnBr_2$). These can react with nicotine to form organometallic complexes.

Useful nicotine salts include, but are not limited to, nicotine pyruvate, nicotine citrate, nicotine aspartate, nicotine lactate, nicotine bitartrate, nicotine salicylate, nicotine fumarate, nicotine mono-pyruvate, nicotine glutamate or nicotine hydrochloride, for example. Preferred nicotine salts include, nicotine lactate, nicotine pyruvate, nicotine citrate, nicotine aspartate, or a combination thereof.

The pH of the first plurality of particles (dissolved in water) may be in a range from about 5 to about 9. Preferably the pH is about 7.0 or higher or in a range from 7.0 to 9.0. A pH of 9 can be reached for a particle without organic acid, while a pH of 5.0 can be obtained with the use of a strong acid or diacid when forming the nicotine salt.

The first plurality of particles may include an amino acid or peptide (preferably formed of three or less amino acids). The amino acid or peptide may reduce adhesion forces of the particles and mitigate or prevent agglomeration of the particles during formation or subsequent handling. The first plurality of particles may form be a free-flowing material and may have a stable relative particle size distribution during processing, transport and storage.

Useful amino acids may include leucine, alanine, valine, isoleucine, methionine, phenylalanine, tyrosine, tryptophan, or a combination thereof. One preferred amino acid is leucine or a leucine isomer, such as L-leucine. A useful peptide includes trileucine, for example.

The plurality of particles may include a sugar or a sugar alcohol. Sugar refers to simple sugars, monosaccharides, disaccharides, and polysaccharides. Without limitation, examples of suitable sugars and sugar alcohols are lactose, sucrose, raffinose, trehalose, fructose, dextrose, glucose, maltose, mannitol, or combinations thereof. Preferred sugars and sugar alcohols include trehalose or mannitol.

The first plurality of particles may contain less than about 30 wt % nicotine. The first plurality of particles may contain about 10 wt % or less nicotine or from about 1 to about 10 wt % nicotine. The first plurality of particles may contain from about 2 to about 7 wt % nicotine or from about 3 to about 7 wt % nicotine, or from about 4 to 6 wt % nicotine, or about 5 wt % nicotine. Nicotine content is calculated based on the total amount of nicotine regardless of the form of nicotine. For example, the first plurality of particles may include 8.4 wt % nicotine salt such as nicotine lactate but the nicotine content is 5 wt %.

The first plurality of particles may contain about 1 to about 20 wt % amino acid. The plurality of particles may contain about 5 to about 15 wt % amino acid. The plurality of particles may contain from about 10 wt % amino acid. The addition of the amino acid, especially L-leucine for example, to the particles may reduce agglomeration or adherence to processing surfaces.

The first plurality of particles may contain about 60 to about 95 wt % sugar. The plurality of particles may contain about 70 to about 90 wt % sugar.

Useful first plurality of particles includes an amino acid being leucine, a sugar being trehalose, and a nicotine salt being nicotine lactate. The nicotine content may be from about 1 to about 10 wt % or about 5 wt %. The leucine content may be from about 5 to about 15 wt % or about 10 wt %. The sugar content may be from about 75 to about 85 wt %.

Useful first plurality of particles includes an amino acid being leucine, a sugar being trehalose, and a nicotine salt being nicotine citrate. The nicotine content may be from about 1 to about 10 wt % or about 5 wt %. The leucine content may be from about 5 to about 15 wt % or about 5 wt %. The sugar content may be from about 75 to about 85 wt %.

Useful first plurality of particles includes an amino acid being leucine, a sugar being trehalose, and a nicotine salt being nicotine pyruvate. The nicotine content may be from about 1 to about 10 wt % or about 5 wt %. The leucine content may be from about 5 to about 15 wt % or about 10 wt %. The sugar content may be from about 75 to about 85 wt %.

Useful first plurality of particles includes an amino acid being leucine, a sugar being trehalose, and a nicotine salt being nicotine aspartate. The nicotine content may be from about 1 to about 10 wt % or about 5 wt %. The leucine content may be from about 5 to about 15 wt % or about 10 wt %. The sugar content may be from about 75 to about 85 wt %.

The first plurality of particles may be formed by: (1) combining a nicotine, and optionally a sugar and an amino acid or peptide in a liquid carrier to form a liquid mixture; (2) spray drying the liquid mixture to form a first plurality of particles having a size in a range from about 0.5 to about 10 micrometres or in a range from about 0.5 to about 5 micrometres; and optionally (3) milling the particles to form first plurality of particles. The milling unit operation may be a fluid energy milling unit operation that reduces the size of the particles.

The liquid carrier may be water, for example. The liquid mixture is flowable. The liquid mixture is configured to flow through an atomization or atomizer nozzle to form a first plurality of particles.

The powder system also includes a second plurality of particles. The second plurality of particles has a particle size that is larger than the first plurality of particles. The second plurality of particles may have a particle size about 20 micrometres or greater, or about 50 micrometres or greater, or about 75 micrometres or greater, or about 100 micrometres or greater. At least 50 vol % of the particles of the second plurality of particles may be about 50 micrometres or greater or are in the range of about 75 to about 200 micrometres. The average particle size of the second plurality of particles maybe in a range between about 75 micrometres and about 150 micrometres. Less than 5 vol % of the particles of the second plurality of particles may be smaller than 20 micrometres. The second plurality of particles may include a flavourant.

The powder system is preferably free-flowing. The first plurality of particles is preferably free-flowing. The second plurality of particles is preferably free-flowing. The powder system contained within the container or capsule is preferably free-flowing. The first plurality of particles contained within the container or capsule is preferably free-flowing. The second plurality of particles contained within the container or capsule is preferably free-flowing.

The powder system may have a stable size distribution. The powder system preferably do not agglomerate to each other. The first plurality of particles preferably do not agglomerate to each other. The second plurality of particles preferably do not agglomerate to each other. The first plurality of particles preferably do not agglomerate to the second plurality of particles. The second plurality of particles preferably do not agglomerate to the first plurality of particles.

The second plurality of particles may be free of nicotine or include a low level of nicotine, such as about 0.1 wt % or less. The second plurality of particles preferably includes no nicotine or only includes trace levels of nicotine. The second plurality of particles may include a flavour component. Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like. Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine component during consumption or inhalation thereof.

Flavourants or flavours refer to a variety of flavour materials of natural or synthetic origin. They include single compounds and mixtures. The flavour or flavourant has flavour properties that may enhance the experience of the nicotine component during consumption. The flavour may be chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Further specific examples of flavours may be found in the current literature, and are well-known to the person skilled in the art of flavouring, for example, of imparting an odor or taste to a product.

Preferably the second plurality of particles includes menthol. For example, second plurality of particles may include from about 1 to about 20 wt % or from about 2 to about 10 wt % or from about 3 to about 6 wt % or about 5 wt % menthol.

Preferably the powder system includes a first plurality of particles about 10 micrometers or less and containing nicotine particles with about 1 to about 15 wt % of a nicotine and in the form of a salt, such as, nicotine lactate, nicotine citrate, nicotine pyruvate, or nicotine aspartate; from about 5 to about 15 wt % of an amino acid such as leucine; a sugar, such as trehalose; and a second plurality of particles about 20 micrometres or greater and containing a flavour component, such as menthol. The powder system preferably comprises a weight ratio of the first plurality of particles to second plurality of particles of about 1:1 to about 10:1, or about 2:1 to about 6:1, or about 3:1 to about 5:1, preferably about 4:1.

The second plurality of particles may include a compound to reduce adhesion forces or surface energy and resulting agglomeration. The second plurality of particles may be surface modified with an adhesion reducing compound to form a coated second plurality of particles. One preferred adhesion reducing compound may be magnesium stearate. Providing an adhesion reducing compound such as magnesium stearate with the flavour particle, especially coating the second plurality of particles or flavour particles, may reduce adhesion forces of the particles comprising flavour and may reduce attraction between flavour particles and thus reduce agglomeration of second plurality of particles or flavour particles. Thus, agglomeration of second plurality of particles with the first plurality of particles may also be reduced. The powder system described herein thus may possess a stable relative particle size of the dual populations of particles when combined. The powder system is preferably free-flowing.

The powder system described herein may form a dry powder composition and be packaged in a container or capsule for consumption. The powder system described herein may form a free-flowing dry powder composition and be packaged or contained in an inhalation delivery consumable element. An inhalation delivery consumable element may be a capsule, for example. The capsule may be by disposed in an inhalation device, such as an inhaler article. The inhalation device may provide for piercing the capsule (at only one end or side of the capsule) and the powder system may be entrained in the inhalation air for delivery to the lungs of a consumer.

The present disclosure further relates to a system including an inhaler article comprising a cavity for receiving a container, such as a capsule, and a piercing element for forming a single aperture in the container or one or more apertures in a single side or end of the container. The container contains a powder system comprising a first plurality of particles having a particle size of about 10 micrometers or less, and a second plurality of particles having a particle size of about 20 micrometers or greater. After the container is pierced with the piercing element, the container has a single aperture or more or more apertures of a diameter of about 0.5 mm to about 1.5 mm that extends through the container. The single aperture or more or more apertures may have an open surface area from about 0.2 mm$^2$ to about 1 mm$^2$, and the container may have a volume from about 0.2 mL to about 0.5 mL, or about 0.3 mL. The container may be a size 2 to size 4, or a size 3 capsule containing from about 20 mg to about 80 mg of a powder system, or from 40 mg to about 60 mg of a powder system, or about 50 mg of a powder system. The first plurality of particles may comprises nicotine or a nicotine salt, an amino acid such as leucine, and a sugar such as trehalose. The amount of nicotine may be about 1 wt % to about 10 wt %, or about 3 wt % to about 7 wt %, or about 5 wt %. The second plurality of particles may comprise a flavour, such as menthol. The powder system comprises a weight ratio of the first plurality of particles to second plurality of particles of about 1:1 to about 10:1, or about 2:1 to about 6:1, or about 3:1 to about 5:1, preferably about 4:1. At least about 50%, or at least about 75%, or at least about 90% of the first plurality of particles may have a particle size of about 5 micrometers or less, or about 3 micrometers or less. At least 50%, or at least about 75%, or at least about 90% of the second plurality of particles may have a particle size of about 50 micrometers or greater, or about 75 to 200 micrometers.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

An inhaler article may include a body extending along a longitudinal axis from a mouthpiece end to a distal end and a capsule cavity defined within the body. The capsule cavity has a cavity length extending along the longitudinal axis. A mouthpiece air channel may extend from the capsule cavity to the mouthpiece end. An end cap may be disposed within the distal end and extends to the capsule cavity. The end cap may extend from an end cap distal end to an end cap inner end. An air channel may extend from the end cap distal end to the end cap inner end. A capsule may have a capsule length and is disposed within the capsule cavity. The capsule length may be in a range from about 25% to about 99% of the cavity length, or about 50% to about 95% of the cavity length, or about 70% to about 90% of the cavity length, or from about 75% to about 85% of the cavity length, or about 80% of the cavity length.

The inhaler article described herein may be combined with a piercing element or piercing device to deliver the powder system to a consumer. The piercing element or piercing device may be separated from or not form a portion of the inhaler article. A plurality of these inhaler articles may be combined with a piercing element or piercing device to form a kit.

The inhaler body may resemble a smoking article or cigarette in size and shape. The inhaler body may have an elongated cylindrical body extending along the longitudinal axis of the inhaler article. The inhaler body may have a substantially uniform outer diameter along the length of the elongated cylindrical body. The inhaler body may have a circular cross-section that may be uniform along the length of the elongated cylindrical body. The inhaler body may have an outer diameter in a range from about 6 mm to about 10 mm, or from about 7 mm to about 10 mm, or about 7 mm to about 9 mm, or about 8 mm. The inhaler body may have a length (along the longitudinal axis) in a range from about 40 mm to about 90 mm, or from about 50 mm to about 80 mm, or about 60 mm to about 70 mm, or 65 mm.

The air channel may be configured to induce a swirling air flow pattern within the capsule cavity of the inhaler body. The air channel may draw inlet air into the capsule cavity of the inhaler body from the end cap distal end. The air channel may induce rotational air flow or swirling air flow as the air flows through the air channels and through the capsule cavity. Air flow through the inhaler device preferably enters the inhaler device at the distal end face or end cap distal end of the inhaler device and moves along the longitudinal axis of the inhaler device to the mouthpiece end. An inlet of the air flow channel may be defined within the end cap distal end face. The end cap distal end face may be orthogonal to the longitudinal axis of the inhaler device. Air flow may not pass thorough the elongated body of the inhaler body. There may be no air inlets through the elongated body of the inhaler body.

The air channel may be a channel element defined along an outer surface of the end cap and extending along a length of the end cap. The end cap may define three sides of the air channel. The end cap may define a bottom surface and opposing depth sides that define a depth of the air channel. The end cap may be inserted into the distal end of the inhaler body and form a portion of the distal end of the inhaler body. The distal end of the inhaler body may surround at least about 75%, or at least about 85% or at least about 90% or 100% of the length of the end cap. The distal end of the inhaler body may contain and hold the end cap in place within the distal end of the inhaler body.

The end cap may be inserted into the distal end of the inhaler body and may be fixed to the inhaler body by friction fit or an adhesive, for example. A distal end portion of the inhaler body may cooperate with the end cap air channel to enclose the air channel or form the remaining top surface of the air channel. The top surface may oppose the bottom surface defined by the end cap. The top surface and bottom surface may be parallel to each other. The opposing depth sides may be parallel to each other. The opposing top surface and bottom surface may be orthogonal to the opposing depth sides.

The air channel may extend a distance along an arc that is co-axial with the longitudinal axis. The air channel may be curved with respect the longitudinal axis of the inhaler device. The air channel may rotate around the circumference of the end cap as a function of a location along the end cap length. The air channel may rotate around about 25% to about 50% of the circumference. The air channel may rotate around the circumference of the end cap an arc length (distance when viewing the end cap from the distal end face) having a central angle (that may be coincident with the longitudinal axis of the inhaler body) in a range from about 45 degrees to about 180 degrees, or from about 45 degrees to about 135 degrees.

The air channel may enter the capsule cavity at an angle relative to the longitudinal axis. The air channel may enter the capsule cavity at an angle in a range from about 5 degrees to about 89 degrees, or about 45 degrees to about 89 degrees, or about 60 degrees to about 89 degrees, or about 70 degrees to about 88 degrees. The air channel may have a first portion parallel with the longitudinal axis and a second portion exiting into the capsule cavity at an angle relative to the longitudinal axis as described above.

The air channel may include at least two or two or more air channels formed into the end cap. The air channel may include at least three, or three or more air channels formed into the end cap. The air channels may be located symmetrically about the end cap. The air channels may oppose each other about the end cap along the end cap length. Preferably the one or more air channels are helical. The helical air channels may be symmetrically disposed along the end cap length and preferably oppose each other along the end cap length. The air channels may each extend a distance along an arc that are each co-axial with the longitudinal axis. The inhaler body may form the top surface for each air channel.

The end cap and air channel defined thereon may be precisely designed and manufactured to impart the desired air flow pattern through the capsule cavity of the inhaler device. This inhaler body and end cap may form a separate piece assembly that may provide for a simple and reliable manufacture and performance of the inhaler device.

The end cap may have an end cap length in a range from about 3 mm to about 12 mm, or from about 4 mm to about 10 mm, or from about 5 mm to about 9 mm, or about 7 mm. The end cap may have an outer diameter sufficient to form a close or friction fit with the inner diameter of the inhaler body. The end cap may have an outer diameter in a range from about 5 mm to about 10 mm, or from about 6 mm to about 9 mm, or about 6.5 mm to about 8.5 mm, or about 7.5 mm.

The end cap may include a collar element having a larger diameter than the remaining body of the end cap. The collar element may function as a physical stop to ensure proper placement of the end cap within the distal end portion of the elongated inhaler body. The collar may abut the elongated inhaler body. The collar may have a diameter that is about 0.5 mm to about 1 mm greater than the diameter than the remaining body of the end cap. The collar element may have a diameter that is substantially similar or the same as the outer diameter of the elongated inhaler body.

The end cap may include a linear piercing channel extending through the length of the end cap. The linear piercing channel may extend along a central axis of the end cap. The linear piercing channel may be co-axial with the longitudinal axis of the inhaler body. The linear piercing channel may be sized to allow a piercing element to pass through the linear piercing channel. The linear piercing channel may have a diameter in a range from about 0.5 mm to about 2 mm.

The end cap may include a resealable element disposed on or within the linear piercing channel. The linear piercing channel includes a first end forming a portion of the end cap distal end and an opposing second end forming a portion of the end cap inner end. The resealable element may be disposed on or within end cap inner end. Alternatively, or in addition, the resealable element may be disposed on or within the end cap distal end.

The resealable element may seal the linear piercing channel. The resealable element may form a hermetic or airtight seal or barrier along the linear piercing channel. The linear piercing channel may be formed of a pierce-able material. A piercing element may pass through the resealable element and puncture the capsule within the capsule cavity. The resealable element may reseal once the piercing element is retracted or removed from the resealable element. Resealable elements or membranes may include a septum or septum-like element. Resealable elements or membranes may be formed of elastic material such as rubber, silicone, metal foil co-laminated with a polymer, or latex and the like.

The capsule cavity may define a cylindrical space configured to contain a capsule (that may have an obround shape). The capsule cavity may have a substantially uniform or uniform diameter along the length of the capsule cavity. The capsule cavity may have a substantially cylindrical or cylindrical cross-section along the length of the capsule cavity. The configuration of the capsule cavity relative to the capsule may allow the capsule to rotate with stability within the capsule cavity. The longitudinal axis of the capsule may rotate with stability about the longitudinal axis of the inhaler body during inhalation. The length of the capsule cavity may form an airtight barrier.

Stable rotation refers to the longitudinal axis of the inhaler body being substantially parallel with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more, or 25 or more, or 40 or more "puffs" by a consumer for a single capsule.

The capsule cavity may have a fixed cavity length. The capsule cavity may have a cavity length of at least about 110% to less than about 300% of the length of the capsule contained therein, or in range from about 110% to about 200% of the capsule length, or from about 120% to about 130% of the capsule length, or about 125% of the capsule length. The capsule may have a length in a range from about 25% to about 99% of the cavity length, or about 50% to about 95% of the cavity length, about 70% to about 90% of the cavity length, or from about 75% to about 85% of the cavity length, or about 80% of the cavity length. The cavity length may be in a range from about 18 mm to about 22 mm and the capsule length may be in a range from about 14 to about 18 mm, or the cavity length may be in a range from about 19 mm to about 21 mm and the capsule length may be in a range from about 15 to about 17 mm, or the cavity length may be about 20 mm and the capsule length may be about 16 mm.

The capsule cavity has a cavity inner diameter, orthogonal to the longitudinal axis, and the capsule has a capsule outer diameter. The capsule outer diameter may be in a range from about 80% to about 99% of the cavity inner diameter, or capsule outer diameter may be in a range from about 85% to about 95% of the cavity inner diameter, or capsule outer diameter may be about 90% of the cavity inner diameter. The capsule outer diameter may be in a range from about 5.4 mm to about 6.4 mm and the cavity inner diameter may be in a range from about 6 mm to about 7 mm, or the capsule outer diameter may be in a range from about 5.7 mm to about 6.1 mm and the cavity inner diameter may be in a range from about 6.4 mm to about 6.8 mm, or the capsule outer diameter may be about 5.85 mm and the cavity inner diameter may be about 6.6 mm.

The capsule cavity may be bounded at an upstream side by the end cap and bounded at a downstream side by a porous support element. The end cap and porous support element cooperate to contain the capsule longitudinally within the capsule cavity. The porous support element may fill the inner diameter of the elongated inhaler body. The porous support element may allow air flow to exhibit a uniform airflow along the cross-section of the elongated inhaler body through the porous support element. The porous support element may function as a diffuser to reduce turbulence effects or edge effects and ensure or maintain the desired air flow pattern through the capsule cavity.

The porous support element may have a length that extends along the longitudinal axis a distance from about 20 mm to about 40 mm, or from about 22 mm to about 35 mm, or from about 25 mm to about 30 mm, or about 27 mm. The porous support element may have an outer diameter sufficient to form a friction fit with the inner diameter of the inhaler body. The porous support element may have an outer diameter in a range from about 5 mm to about 10 mm, or from about 6 mm to about 9 mm, or about 6.5 mm to about 8.5 mm, or about 7.5 mm.

The porous support element may define a filter element. The filter element may be formed of a network of fibres. The network of fibres may be a nonwoven fibre element. The porous support element may be a plug of filtration material. Fibres forming the porous support element may be derived from polylactic acid. Fibres forming the porous support element may be cellulose acetate. The filter element may be a plug of cellulose acetate or a plug of polylactic acid. The porous element may comprise a plastic mesh. The plastic mesh may have holes of from about 1 $mm^2$ to about 4 $mm^2$ or of about 2 $mm^2$.

The capsule may be sealed within the inhaler article prior to consumption. The inhaler article may be contained within a sealed or airtight container or bag. The inhaler article may include one or more peelable seal layers to cover the one or more air inlet channels or the air outlet or mouthpiece of the inhaler article.

A separate piercing element, such as a metal or rigid needle, may form a single aperture (only a single aperture) through the capsule received in the capsule cavity. The piercing element may pass through the resealable element sealing the piercing channel on the end cap.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free-flowing powder. Thus, the inhaler article may not require the elevated inhalation rates typically utilized by conventional inhalers to deliver the nicotine particles described above deep into the lungs.

Rotation of the single aperture capsule within the inhaler body may aerosolize the nicotine particles or powder system and may assist in maintaining a free-flowing powder. Thus, the inhaler article may not require the elevated inhalation rates typically utilized by conventional inhalers to deliver the nicotine particles described above deep into the lungs.

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIG. 7 is a schematic diagram end view of a capsule with the single aperture The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 1:
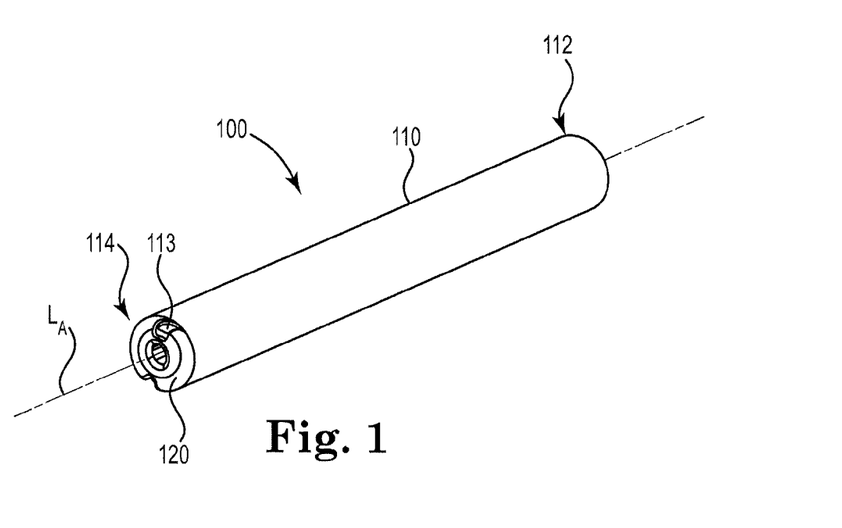
FIG. 1 is a perspective view of an illustrative inhaler article.
Figure 2:
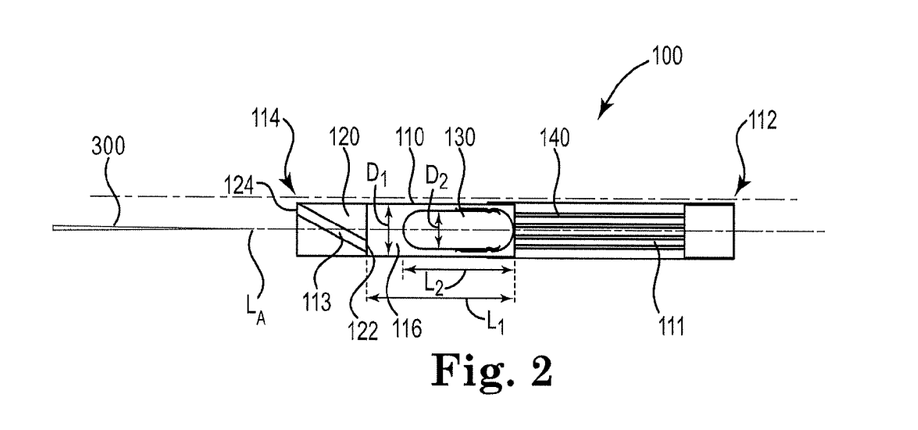
FIG. 2 is a cross-sectional schematic diagram of the illustrative inhaler article of FIG. 1 along the longitudinal axis.
Figure 3A:
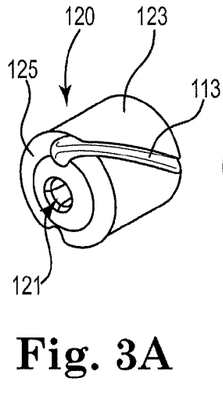
FIG. 3A and FIG. 3B are perspective views of an illustrative end cap.
Figure 3B:
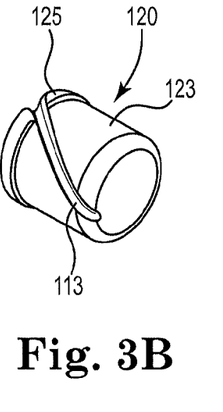

FIG. 1 and FIG. 2 illustrate an example of an inhaler article 100. FIG. 2 is a cross-sectional schematic diagram of the illustrative inhaler article of FIG. 1 along the longitudinal axis. The inhaler article 100 includes a body 110 extending along a longitudinal axis $L_A$ from a mouthpiece end 112 to a distal end 114 and a capsule cavity 116 defined within the body 110. A mouthpiece air channel 111 extends from the capsule cavity 116 to the mouthpiece end 112. An end cap 120 is disposed within the distal end 112 and extends to the capsule cavity 116. The end cap 120 extends from an end cap distal end 124 to an end cap inner end 122 an end cap length. The end cap 120 includes an air channel 113 extending from the end cap distal end 124 to the end cap inner end 122. The air channel 113 is non-parallel with the longitudinal axis $L_A$.

The end cap inner end 122 and a porous support element 140 bound the capsule cavity 116. A capsule 130 is disposed within the cavity 116. The capsule 130 contains the powder system. The end cap 120 and the porous support element 140 cooperate to contain the capsule 130 longitudinally within the capsule cavity 116. The mouthpiece end 112 is illustrated having a recessed end where the body 110 bounds an open space at the mouthpiece end 112. Alternatively, the porous support element 140 can extend to the mouthpiece end 112 to fill the entire mouthpiece end 112.

The capsule cavity 116 has a cavity length $L_1$ extending along the longitudinal axis $L_A$. The capsule 130 has a capsule length $L_2$. The capsule cavity has a cavity inner diameter $D_1$. The capsule 130 has a capsule outer diameter $D_2$. The capsule 130 axis of rotation may be coextensive with the longitudinal axis $L_A$.

FIG. 3A to FIG. 4B illustrate opposing curved, or helical air channels 113 rotating about the circumference as a function of a location along the length of the end cap 120. The end cap 120 may include a collar element 125 having a larger diameter than the remaining body 123 of the end cap 120.

FIG. 3A, FIG. 4A, FIG. 5 and FIG. 6 illustrate a linear piercing channel 121 extending through the length of the end cap 120. The linear piercing channel 121 may extend along a central axis of the end cap 120.

Figure 4A:
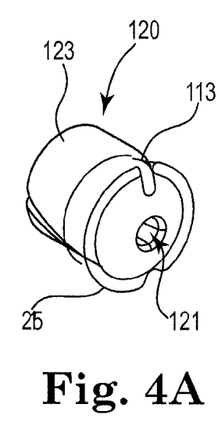
FIG. 4A and FIG. 4B are perspective views of another illustrative end cap.
Figure 4B:
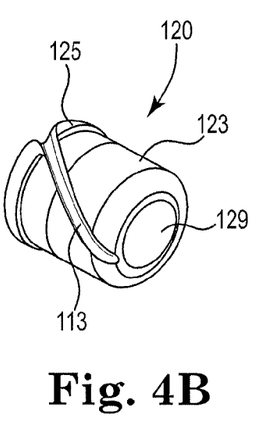
Figure 5:
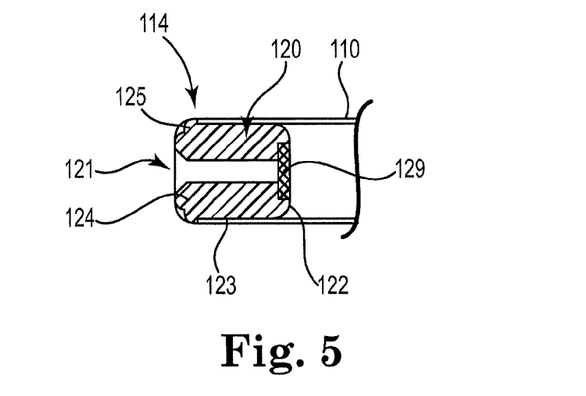
FIG. 5 is a cross-sectional schematic diagram of another illustrative end cap.
Figure 6:
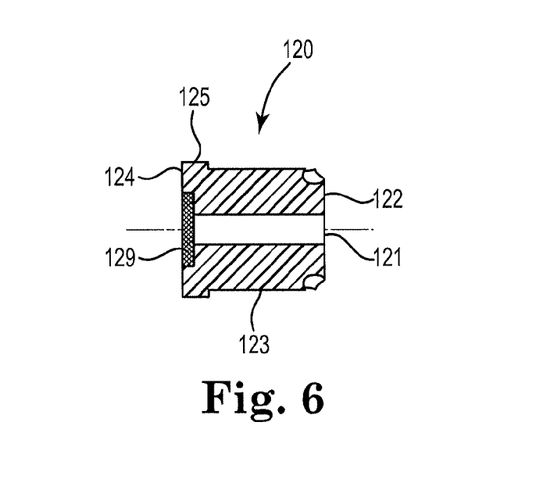
FIG. 6 is cross-sectional schematic diagram of another illustrative end cap.

FIG. 4B, FIG. 5 and FIG. 6 illustrate a resealable element 129 disposed on or within the linear piercing channel 121. FIG. 4B and FIG. 5 illustrate a resealable element 129 disposed on the end cap inner end 122 and sealing the linear piercing channel 121. FIG. 6 illustrates a resealable element 129 disposed on the end cap distal end 124 and sealing the linear piercing channel 121.

Figure 7:
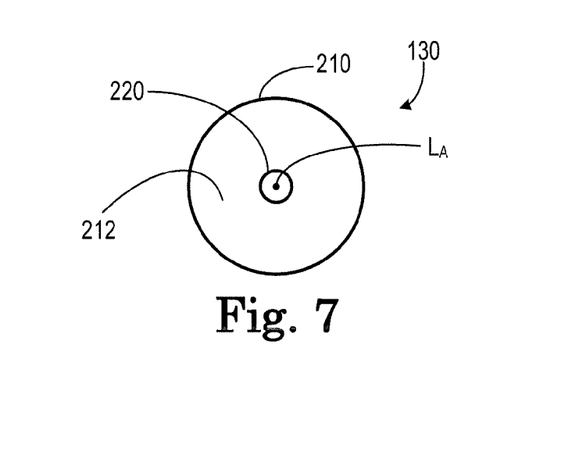

FIG. 7 is a schematic diagram end view of a capsule 130 with only a single aperture 220. The single aperture 220 may extend though the capsule body 210 at an end portion 212 of the capsule body 210. The single aperture 220 may be incident with a longitudinal axis of the capsule 130 and incident with the longitudinal axis $L_A$ of the inhaler body 110.

A separate piercing element 300 (FIG. 2) may be utilized by a consumer to pierce the capsule 130 and form the single aperture 220 through the piercing channel shown in FIG. 1 in the end cap 120 along the longitudinal axis $L_A$. The piercing element may be withdrawn from the single aperture 220. A consumer may then utilize the capsule 130 in an inhaler device 100.

EXAMPLES

The following non-limiting examples provide examples of nicotine powder formulations in accordance with various aspects of the present disclosure and illustrate properties, including size and nicotine delivery, associated with the formulations.
Nicotine Delivery Example The impact on nicotine delivery of mixing the first plurality of particles (nicotine powder) with the second plurality of particles having a larger particle size is tested. The test sample (Example 7) includes both the first plurality of particles (40 mg) and the second plurality of particles (10 mg). The control sample (Example 7C) includes only the first plurality of particles (40 mg). Nicotine delivery is tested for varying numbers of puffs. The results are shown in Table 9 below.
Sample Preparation:

The first plurality of particles is prepared with nicotine lactate, trehalose, and leucine, and includes 5 wt % nicotine (based on the total weight of nicotine in the nicotine lactate). The powder is prepared by spray drying, and has a particle size $X_{50}$ of 2.25±0.2 micrometres.

The second plurality of particles has a particle size $X_{50}$ of 100 micrometres and includes no more than 5% of the particles with a particle size of 20 micrometres or less. The powder includes 4.3 wt % menthol.

The powder system or mixture of Example 7 is prepared by mixing the first plurality of particles (40 mg) with the second plurality of particles (10 mg) at a weight ratio of 4:1, the total weight of the powder mixture is 50 mg.

Samples are prepared for testing by packing 40 mg of the first plurality of particles (control, Example 7C) and 50 mg of powder system (test sample, Example 7) into size #3 HPMC capsules. Four replicates of each sample are prepared and tested. The capsules are inserted into inhalers and pierced once with a 1 mm diameter needle forming only a single aperture.
Testing:

The samples are "smoked" at a suction rate of 80 mL/2 sec with a 30 sec interval between puffs, and the powder delivered from the inhaler is collected in groups of 4 puffs from the first 20 puffs, and in groups of 10 puffs thereafter. The amount of nicotine in the collected puffs is tested by gas chromatography. The results for nicotine delivered in the first 12 puffs, the first 20 puffs, and the first 50 puffs is shown in Table 9 below. The amount of nicotine is averaged for the four replicates and normalized for the quantity of nicotine present in the powder.

TABLE 9

| | Nicotine Delivery | | |
|---|---|---|---|
| Example | 1-12 Puffs | 1-20 Puffs | 1-50 Puffs |
| 7C (control) | 0.20 | 0.36 | 0.61 |
| 7 | 0.51 | 0.68 | 1.08 |

The content of a container according to the invention comprising a powder system according to the invention is more fully delivered over a series of inhalations.

The invention claimed is:

1. A container containing a powder system comprising:
 a first plurality of particles having a mass median aerodynamic diameter particle size of about 10 micrometers or less;
 a second plurality of particles having a mass median aerodynamic diameter particle size of about 20 micrometers or greater;
 wherein the powder system comprises a weight ratio of the first plurality of particles to second plurality of particles of about 1:1 to about 10:1, and
 a single aperture extending through the container,
 wherein the container is a capsule and the single aperture extends through a capsule endcap and the capsule comprises a longitudinal axis and the single aperture is incident with the longitudinal axis, and wherein the single aperture has a diameter of about 0.5 mm to about 1.5 mm, or an open surface area of the single aperture is in a range from about 0.1% to about 0.5% of the total surface area of the container, and wherein the container is configured to release at least 10 uniform fractional amounts of the powder system.

2. The container according to claim 1, wherein the first plurality of particles comprises nicotine or a nicotine salt.

3. The container according to claim 1, wherein the first plurality of particles comprises an amino acid comprising leucine.

4. The container according to claim 1, wherein at least 90%, of the first plurality of particles have a mass median aerodynamic diameter particle size of about 5 micrometers or less.

5. The container according to claim 1, wherein at least 90%, of the second plurality of particles have a mass median aerodynamic diameter particle size of about 50 micrometers or greater.

6. The container according to claim 1, wherein the single aperture has an open surface area from about 0.5 mm$^2$ to about 1 mm$^2$, and the capsule has a volume from about 0.2 mL to about 0.5 mL.

7. The container according to claim 1, wherein the first plurality of particles comprises nicotine lactate, leucine, and a sugar comprising trehalose, and has a nicotine content of about 1 wt % to about 10 wt %.

8. The container according to claim 1, wherein the capsule is a size 2 to size 4 capsule and contains from about 20 mg to about 80 mg of powder system.

9. The container according to claim 1, wherein the second plurality of particles comprises a flavour, the flavour comprises menthol.

10. The container according to claim 1, wherein at least 90% of the first plurality of particles have a mass median aerodynamic diameter particle size of about 3 micrometers or less, and at least 90% of the second plurality of particles have a mass median aerodynamic diameter particle size in a range from 75 to 200 micrometers, and the powder system comprises a weight ratio of the first plurality of particles to second plurality of particles of about 2:1 to about 6:1.

11. The container according to claim 10, wherein the first plurality of particles comprises nicotine lactate, leucine, and a sugar comprising trehalose, and has a nicotine content of about 1 wt % to about 10 wt %.

12. The container according to claim 11, wherein the first plurality of particles comprises nicotine lactate, 5 to 15 wt % leucine, and 75 to 85 wt % sugar comprising trehalose, and has a nicotine content of about 1 wt % to about 10 wt %.

13. The container according to claim 10, wherein the second plurality of particles comprise menthol.

14. The container according to claim 10, wherein the single aperture has an open surface area in a range from about 0.2% to about 0.5% of the total surface area of the container and the container is a size 3 capsule containing 40 to 60 mg of powder system.

15. The container according to claim 1, wherein the capsule comprises an upstream capsule endcap and a downstream capsule endcap and the single aperture extends through the upstream capsule endcap.

16. The container according to claim 1, wherein an open surface area of the single aperture is in a range from about 0.1% to about 0.5% of the total surface area of the container, and wherein the capsule has a volume from about 0.2 mL to about 0.5 mL.

17. A system comprising:
the container according to claim 1; and
an inhaler article comprising:
a cavity for receiving the container; and
a piercing element for forming a single aperture in the container.

18. The system according to claim 17, wherein the cavity is bounded on an upstream end by an end cap providing inhalation airflow that rotates the container within the cavity, and the cavity is bounded on a downstream end by a porous element that contains the container and transmits particles entrained within the inhalation airflow to a mouthpiece of the inhaler.

19. The system according to claim 18, wherein the piercing element pierces the end cap and only one capsule endcap to form the single aperture.

20. The system according to claim 17, wherein the inhaler delivers a substantially uniform dose of the powder system over each of at least about 20 inhalation puffs.

* * * * *